United States Patent [19]

Clupper

[11] Patent Number: 5,583,590
[45] Date of Patent: * Dec. 10, 1996

[54] ALERT MONITORING SYSTEM

[75] Inventor: Harold E. Clupper, West Chester, Pa.

[73] Assignee: Wabash Scientific Corp., West Chester, Pa.

[ * ] Notice: The terminal 14 months of this patent has been disclaimed.

[21] Appl. No.: 877,709

[22] Filed: May 4, 1992

[51] Int. Cl.$^6$ .............................. A61B 3/00; A61B 5/04; G02C 1/00
[52] U.S. Cl. ................. 351/200; 351/209; 351/158; 128/733; 128/745; 340/573; 434/258
[58] Field of Search .................... 351/158, 209, 351/210, 41, 200; 128/733, 745; 434/238, 258; 340/573, 574, 576, 686, 689

[56] References Cited

U.S. PATENT DOCUMENTS

| | | | |
|---|---|---|---|
| 2,902,030 | 9/1959 | Kennedy et al. | 128/733 |
| 3,542,457 | 11/1970 | Balding | 351/209 |
| 3,689,135 | 9/1972 | Young et al. | 351/246 |
| 3,850,511 | 11/1974 | Merchant | 351/209 |
| 3,946,723 | 3/1976 | Servos | 128/733 |
| 4,303,394 | 12/1981 | Berke et al. | 434/40 |
| 4,474,186 | 10/1984 | Ledley et al. | 128/733 |
| 4,561,448 | 12/1985 | Buchas | 128/733 |
| 4,576,184 | 3/1986 | Westerman | 128/733 |
| 4,582,403 | 4/1986 | Weinblatt | 351/210 |
| 4,585,011 | 4/1986 | Broughton et al. | 128/745 |
| 4,595,017 | 6/1986 | Semenov et al. | 128/745 |
| 4,836,219 | 6/1989 | Hobson et al. | 128/782 |
| 4,863,259 | 9/1989 | Schneider et al. | 351/210 |
| 4,967,186 | 10/1990 | Ludmirsky et al. | 351/210 |
| 5,180,907 | 1/1993 | Udden et al. | 351/210 |

FOREIGN PATENT DOCUMENTS

| | | | |
|---|---|---|---|
| 0464303 | 3/1975 | U.S.S.R. | 351/209 |
| 0625687 | 8/1978 | U.S.S.R. | 351/209 |
| 0820797 | 4/1981 | U.S.S.R. | 351/209 |

OTHER PUBLICATIONS

Young et al.; "Methods & Designs Survey of Eye Movement Recording Methods"; Behavior Research Methods & Instrumentation; vol. 7(5); 1975 pp. 397–429.

*Primary Examiner*—Ricky D. Shafer
*Attorney, Agent, or Firm*—Rene A. Kuypers

[57] ABSTRACT

A system for monitoring alertness of a human while performing certain tasks. Alertness is detected herein by determining the tracking ability of the eye with respect to a visual disturbance, and is measured with respect to head motion. A decision circuit is provided when the motor response of the eye is deemed to be impaired as a result of drowsiness, inattention, or substance abuse.

13 Claims, 3 Drawing Sheets

EYE POSITION, $e_1$

HEAD POSITION, $e_2$ $e_1-e_2$

LIMIT DETECTOR OUTPUT, $e_3$

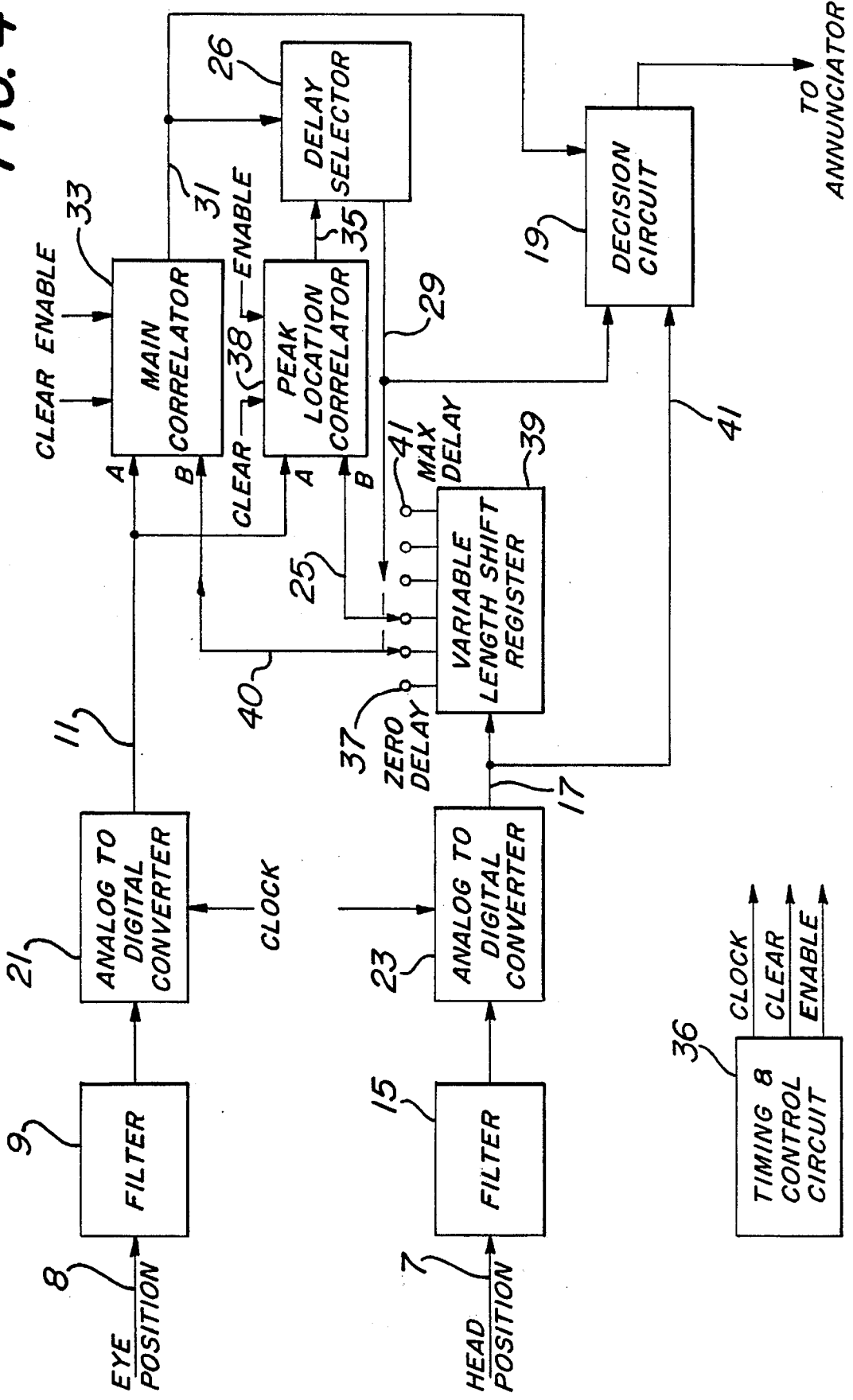

ALERT MONITORING SYSTEM

BACKGROUND OF THE INVENTION

The invention relates in general to a system that measures the ability of the eye to track an object and in particular the ability of the eye to fixate steadily upon an object while the head is undergoing normal random motion in three axes.

A servo system is one in which the desired response is compared to the actual response and the difference or error is applied to the driving means in such a way as to reduce the error to zero. It is the purpose of this invention to treat the eye-positioning mechanism as a servo system and to measure the quality of this system in much the same way as in an electro-mechanical servo system.

In prior art publications related to human performance, it has been noted that the measurement of alertness required that the subject perform some structural mental activity requiring concentration. However, these techniques are not suitable when the subject is performing a real world task that requires full attention, such as driving a vehicle.

Other techniques such as using infrared or other sensors to passively monitor the activity of the eyelid or eyeball are not satisfactory because they fail to take into account the normal movement of these elements in response to the motion of the head and other normal visual processes. They also fail to provide a rapid indication of visual disfunction.

Another prior art system utilizes eyeblink waveforms for detecting the onset of drowsiness. These systems require a history of eyeblinks in order to detect a deviation from the normal. This limits a rapid response of the system necessary to avoid, for example, vehicular accidents.

The basis of the present invention is to measure and evaluate the motion of the eye with respect to the head. In the alert human being, whenever the eye is open it is fixating on an object or detail of interest. If the head moves while fixating on an object, the perceived image will start to shift which generates a small error. In response to this error, the oculomotor system positions the eye in the precise amount necessary to keep this error near zero so that the image appears stable.

Under the conditions of fatigue, inattention or substance abuse, the observed scene will move or jitter in response to head motion. This is the result of a transient inability to reduce the error to zero.

The present invention is therefore different from known prior art systems in that is based upon servo system principles which can be readily measured and evaluated. Normal visual artifacts, such as the relatively slow motion of the observed object or saccadic motion (the rapid jump made by the eye when moving from one detail to another) are removed during the evaluation.

SUMMARY OF THE INVENTION

The invention comprises an alertness monitor having certain transducer instrumentation to measure an angular position of the eye about a horizontal axis through its center and, a transducer to measure the angular position of the head about the same axis. Signals representing the angular positions of the head and eye are sent to a computational circuit where they are scaled and filtered to remove normal artifacts. The output of the computational circuit is a function of the similarities of the two signals in both amplitude and phase that occur when the eye is accurately tracking an object. On the other hand, any finite differences in the signals can be attributed to poor tracking due to drowsiness, inattention, or substance abuse. An annunciator may provide an audible warning to an operator or other third party when such a state occurs.

BRIEF DESCRIPTION OF THE DRAWINGS

FIG. 4 is a more detailed diagram of the computational block represented in FIG. 2.

DESCRIPTION OF THE PREFERRED EMBODIMENT

Figure 1:
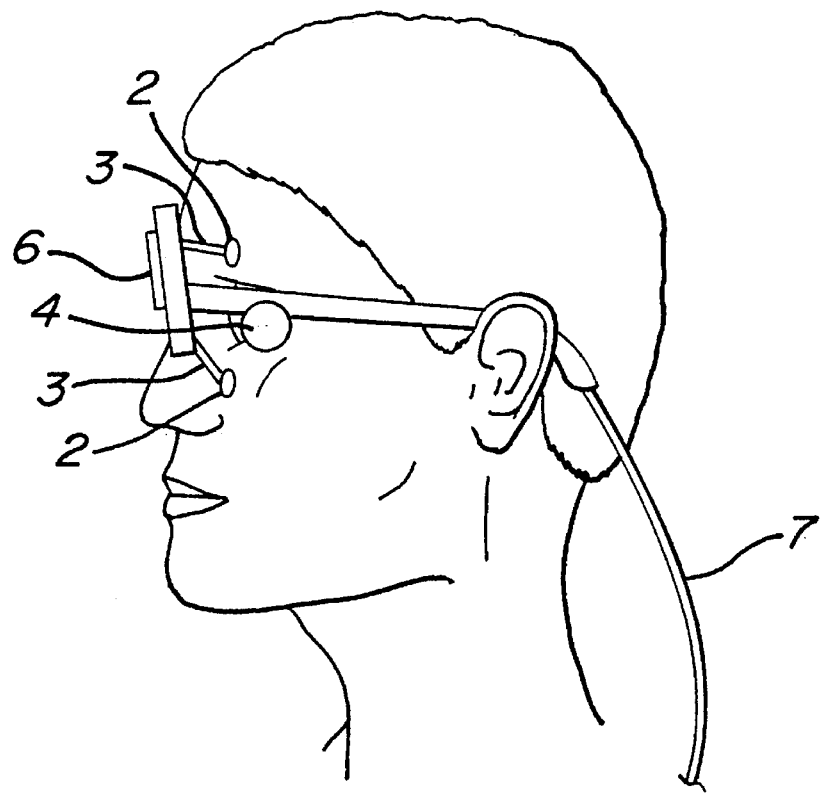
FIG. 1 is a facial side view of a person wearing a partial eye frame for holding and positioning a pair of sensor electrodes for detecting eye position and a device for detecting head position.
Figure 1A:
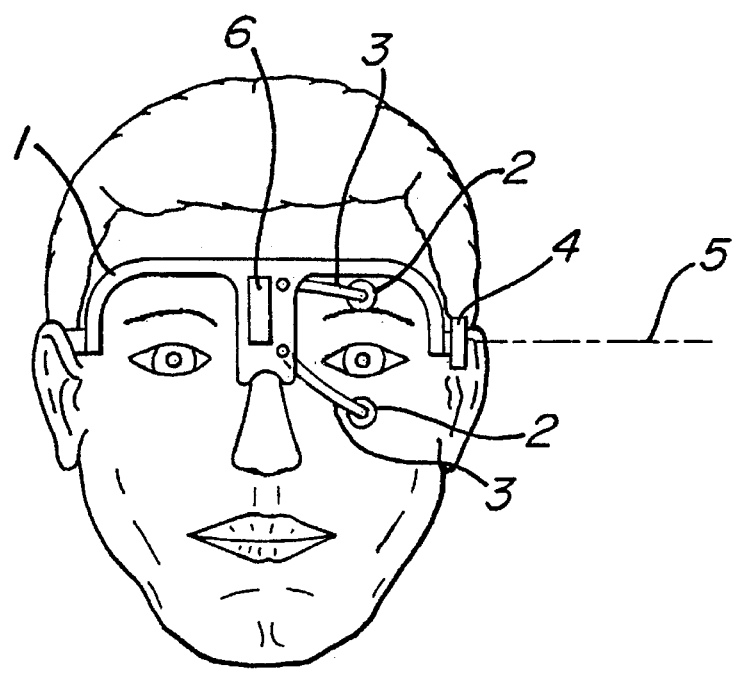
FIG. 1A is a facial front view of the apparatus worn by a person in FIG. 1.

Referring now to the drawings and in particular to FIGS. 1 and 1A, there is depicted a partial eye frame 1 to provide a mounting and positioning member for a pair of attached biopotential sensor electrodes 2 and an angular head position transducer 4. The frame 1 is arranged so as not to obscure the normal field of vision and is fabricated from a conductive material to make contact with the skin. This contact provides a ground reference for the biopotential measurements which are to be taken.

The electrodes 2 which are made of conductive polymers, gels, or woven stainless steel mesh are mounted at the ends of compliant spring strips 3. When the frame 1 is placed on the head, the spring strips 3 position the electrodes 2 to contact the skin above and below the eye and hold them in place with a light force of a few grams. When positioned in this manner, the electrodes 2 will detect the voltage generated by the muscles which control the movement of the eyeball about a horizontal axis 5. This voltage is in the range of 0.1 to 3.5 millivolts and is directly proportional to the position of the eye. The spring strips 3 also provide a electrical connection between the electrodes 2 and the input terminals A, B of a high-gain differential amplifier 6 which amplifies the low level analog voltages resulting from the rotation of the eye about the horizontal axis 5. The amplified output signal emanating from amplifier 6 passes through cable 7 to an external circuit (not shown). This circuit will be discussed in greater detail hereinafter.

Transducer 4 which is an electrolytic position sensor measures the angular position of the head about the horizontal axis 5; that is, the transducer 4 is mounted with its sensitive axis along the same horizontal axis 5 about which the eye rotates. The output signal from the position sensor 4 passes through cable 7 to an external circuit (not shown). This circuit will be discussed in greater detail hereinafter. The transducer 4 is a well known device variously described as tilt meter or electrolytic potentimeter comprising in this instance a glass vial of toroidal shape partially filled with an electrolyte so as to make a bubble and containing electrodes to sense the location of the bubble. Such devices are referenced in U.S. Pat. No. 4,536,967 and manufactured by Spectron of Hauppauge, N.Y. and the Fredericks Company of Huntingdon Valley, Pa. and others. In this application, the electrolyte within the toroidal enclosure is overfilled with a nonconductive fluid of a specific gravity slightly less than that of the conducting electrolyte. This makes the sensor insensitive to accelerations in any plane except about the sensitive axis 5.

Figure 2:
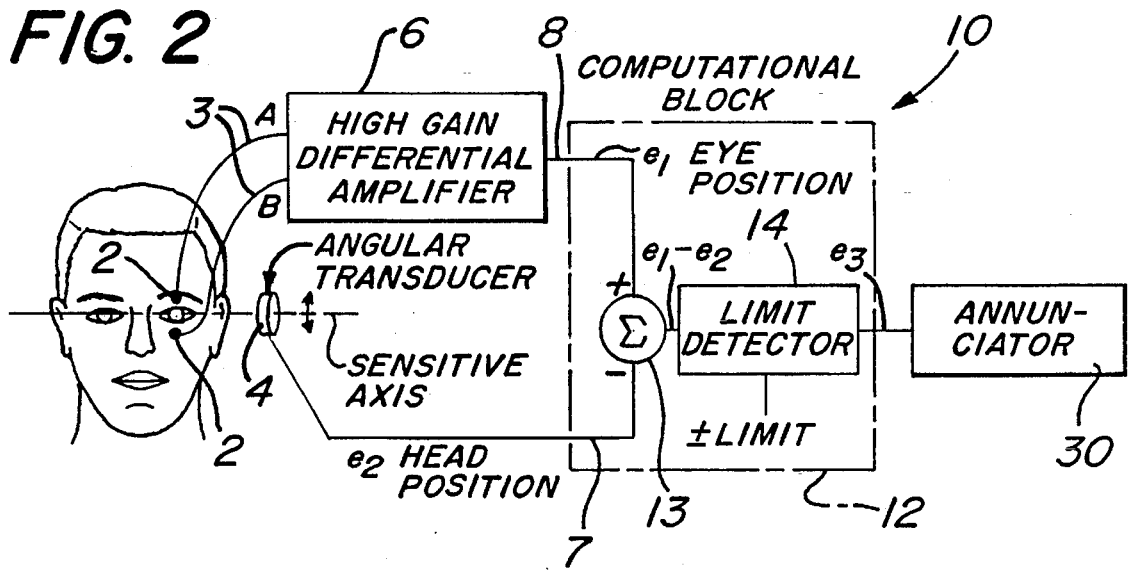
FIG. 2 is a block diagram for operating upon the information generated by the eye and head positioning device to generate a signal that indicates eye impairment.

FIG. 2 illustrates the circuitry in block diagram form to explain the operating principles of the system under a condition of simply-closing the eyelid which is one simple way of destroying a fixation. The elements of the block circuitry 10 comprises the high gain differential amplifier 6 in combination with a computational block 12 which includes a limit detector 14, a bi-stable element and a summing circuit 13. The output of the limit detector is directed into an annunciator 30 for warning the user of the monitor system that he/she is not alert to their surroundings.

The invention is based upon the ability of the eye to fixate steadily upon an object while the head is undergoing random motion. In effect, the eye in combination with the movement of the head is a servo system in which the desired response is compared to the actual response and, the difference of the error is applied to the driving means which reduces the error to zero. Whenever the eye is open it is fixating on an object of interest. If the head moves while fixating on an object of interest, the perceived image will start to shift, generating a small error. In response to the error, the eye is driven the precise amount necessary to keep the error near zero and thus the image will appear stable. Under conditions of fatigue, inattention, or substance abuse, the observed scene will move in response to head motion. This is the result of an inability to reduce the error to zero. The circuit of FIG. 2 illustrates one simple way to measure the magnitude of the error and to generate a signal when the error exceeds a given magnitude as will be discussed hereinafter.

The signals generated by the angular position of the eye when fixating upon an object or detail of interest is a bipolar position signal which is directed into a high gain differential amplifier 6. The output of the amplifier 6 is designated as e1, and is identified in FIG. 3A. The movement of the head while the eyes are fixating is measured by the angular transducer 4 which generates a head position signal which is identified as e2 and is depicted in FIG. 3B. The output e1 of the amplifier 6 and the output e2 emanating from transducer 4 are directed into the circuit 13 of the computational block which compares e1 and e2. The circuit 13 subtracts the e2 from the e1 as shown in FIG. 3C, and the result is sent to the receiver or detector 14. The detector 14, which includes a bi-stable member, provides upper and lower limits about a zero level such that when the limits are not exceeded its output e3 remains in an unenergized of OFF state as indicated in FIG. 3D of the drawings. Since the output signal e3 is in an OFF state, it will not activate the annunciator or alarm device 30 which indicates that the eyes are properly fixating upon an object.

Figure 3A:
FIGS. 3A, 3B, 3C, and 3D represent typical signals produced at various points of the block diagram shown in FIG. 2.
Figure 3B:
Figure 3C:
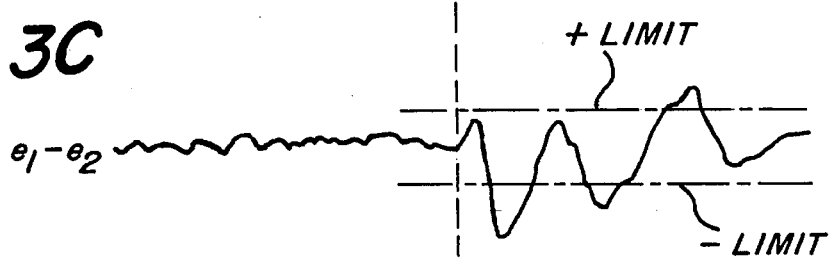
Figure 3D:
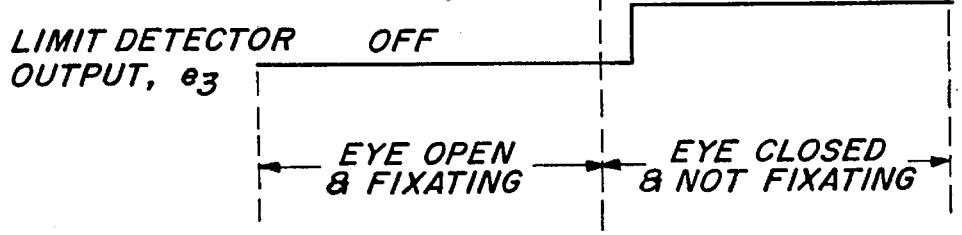

In the event that the eyes are not fixating upon an object, the eye signal e1 will appear as shown in FIG. 3A to the right of the dotted vertical line. This signal e1 indicates that the person under observation is not fixating upon an object as a result, for example, of intoxication. The head position signal indicating a random up and down movement of the head and is indicated in FIG. 3B. The difference between the signals e1 and e2 is illustrated on FIG. 3C where the limit parameters are defined. Once the limits are exceeded by the resulting signal, a one-shot multivibrator within the limit detector is activated or turned ON as shown in FIG. 3D.

A detailed implementation of the preferred embodiment of the computational block of FIG. 2 is shown in FIG. 4. In the detailed circuit of FIG. 4, the eye and head position signals are directed into respective filters 9 and 15 and thence to analog to digital convertors 21,23. The computational block consists of circuitry to perform a time domain cross-correlation function which is a conventional technique for detecting signals buried beneath a blanket of similar signals and noise. The cross-correlation circuit essentially comprises a main correlator 33, a peak location correlator 38, and a delay selector 26; one of the inputs to the correlator circuits 33,38 emanates from the variable length shift registers 39. The output of the cross-correlation circuits are applied to the input of a decision circuit 19, and whose output signal is directed to the annunciator as in FIG. 2.

It should be noted that the desired myoelectrical (i.e., voltages generated by the muscles of the body) signal from the eye is in the range of a few hundred microvolts. When this signal is amplified, other elements, such as noise, offset and drift in addition to the desired signal will be produced. Also superimposed upon the desired tracking signal from the eye are voltages from the eyelid and other facial muscles. A major perturbation results from the saccadic movement of the eye. The saccade is the rapid jump made by the eye as it moves from fixating on one detail of the scene to fixating on another detail. This introduces a sudden shift in the baseline of the desired tracking signal and must be removed by the computational block. In view of the characteristics of the above mentioned electrical signals, the use of time domain cross-correlation techniques are being utilized. A single point on a correlation function is the average of the product of the two time functions. Therefore, any spurious signals caused by eyeblinks, noise, or saccadic movement are averaged out since they will not be accompanied by a corresponding variation in the other input. The desired signals will accordingly be recovered from accompanying noise.

Although the block diagram of FIG. 4 is shown by use of discrete functions, all computations can be accomplished by a single-chip microprocessor such as Motorola MC 146805G2 which is a low-power CMOS device suitable for battery operation. Circuit 36 generates the normal housekeeping functions of clear, enable and clock which are applied to converters 21,23 and correlators 33,38 for purposes of proper timing and control during operation. The analog eye position signal 8 is directed into a filter 9 which allows only a smoothed AC portion of the original signal to pass; in addition, the filter 9 removes any slowly varying component that may result from a differential change in the electrode potentials at the skin surface. This processed AC signal is then directed to an analog-to-digital (A/D) converter 21 and the resulting digital signal 11 applied to input A of the main correlator 33 and to input A of the peak location correlator 38.

The analog head position 7 is directed into a filter 15 which is similar to filter 9 except that the rejection of the slowly varying component is designed to reduce changes in the electrolytic angular position sensor output due to average head orientation. The output of the filter 15 is directed to an analog-to-digital converter 23 which is identical to A/D converter 21. The resulting digital signal 17 is applied to the variable length shift register 39 and to a decision circuit 19. The signal 17 is sent to the shift register 39 since the signal describing the eye position 11 will always lag the head position signal 17 and, therefore, a time delay is introduced into the head position signal in order to establish the optimum correlation between these signals.

The optimum correlation is achieved by directing the head position signal 17 to a variable length shift register 39 which stores digital values amounting to the last several seconds of head movement where the shift register is clocked at the same rate as the A/D converter 23. For the purposes of this description, the shift register 39 is shown schematically as a conventional device with several switch selectable outputs located at zero delay 37 and successive delays along multiple stages up to a maximum delay 41. Output 40 from the variable length shift register 39 is fed into the second input B of the main correlator 33; also, output 25 from the variable shift register 39 is delayed a fixed amount from output 40 and is fed into the second input B of the peak location correlator 38.

As understood in the art, the cross-correlation block 33 provides an average of the product of the two time functions representing the eye and delayed head position. Thus, a single point on the correlation function is an average of the above-stated product; hence, any spurious signals caused by the eyeblinks, noise or saccadic movement are averaged out since they will not be accompanied by a corresponding variation in the other input. The magnitude of the correlation function indicates the similarities of the two signals and the degree to which the eye is tracking an object. On the other hand, any finite differences in the signals can be attributed to poor tracking due to drowsiness, inattention, or substance abuse.

The delay selector 26 continuously monitors the amplitudes of the correlation function from the correlators 33 and 38 in order to find the peak nearest zero delay. The output 35 of the peak location correlator 38 as well as output 31 of main correlator 33 are directed to a delay selector 26. The delay selector 26 continuously modifies the delay of the variable shift register 39 to maximize output 31 with output 35 providing the information as to whether the delay should be increased or decreased. This delay signal 29 is sent to the decision block 19 along with the signal 17 representing the magnitude of the head motion and the main correlator signal 31. The decision block 19 contains comparators (subtractors) and limits for examination of signals 31, 29, and 17 and provides an annunciator output when the signals fall outside the limits. If the delay in the response of the eye as indicated by the magnitude of the delay signal 29 exceeds a predetermined limit, the annunciator is activated. In addition, the annunciator is activated if the main correlator output 31 falls below a second limit indicating poor tracking function. This second limit is determined by computing the average motion of the head from the head position signal 17. By performing this simple computation, the decision block will provide an accurate indication for all ranges of activities from sedentary to active. Other algorithms similar to the above are possible in order to tailor the response for a given range of tasks.

This invention has been described by reference to precise embodiments, but it will be appreciated by those skilled in the art that this invention is subject to various modifications and to the extent that those modifications would be obvious to one of ordinary skill they are considered as being within the scope of the appended claims.

What is claimed is:

1. An alert monitoring system for use by a person in order to detect drowsiness, inattention, or substance abuse comprising, a.) means juxtaposed to certain facial areas for respectively detecting positions of the person's eyes and head when the eyes are fixating upon a viewed object, b.) said juxtaposed means allowing said person to freely move in all directions wherein said juxtaposed means includes an appliance for positioning in the vicinity of the eyes, and c.) said appliance comprising a frame means including ear pieces to provide mounting and positioning means for first and second sensing means, d.) said first sensing means comprising biopotential electrodes which are in physical contact with the face above and below the eye, e.) said first and second sensing means located upon said juxtaposed means for generating first and second signals respectively based upon a fixation of the eyes upon said viewed object and the position of the head with respect to the fixation;

f.) means for combining said first and second signals to generate a third signal, g.) said third signal providing an indication that the eyes are fixating or not fixating upon said viewed object;

h.) means for receiving said third signal to determine whether it is within or outside a defined limit, i.) such that when the eyes are not fixating upon said object said third signal is outside said limit, j.) whereby the person is deemed to be impaired due to said drowsiness, inattention, or substance abuse, and k.) when the eyes are fixating upon the object, said third signal is within said limit and the person is not impaired.

2. An alert monitor system in accordance with claim 1 wherein said second sensing means comprises an angular position sensor located along a horizontal axis about which the eye rotates in response to vertical motion of the head.

3. An apparatus in accordance with claim 1 wherein said means for receiving said third signal comprises a limit detector.

4. An apparatus in accordance with claim 3 wherein said limit detector comprises a bi-stable means.

5. An alert monitoring system for use by a person in order to detect drowsiness, inattention, or substance abuse comprising a.) means juxtapositioned to certain facial areas for respectively detecting positions of the person's eyes and head, b.) said juxtaposed means allowing said person to freely move in all directions, c.) said juxtaposed means including means for generating first and second signals respectively based upon a fixation of the eyes upon a viewed object and the position of the head with respect to the fixation, and said first signal lagging said second signal;

d.) means for applying a delay to said second signal with respect to said first signal to optimize said signals with respect to one another such that said lagging is minimized, and said means for applying a delay permitting delays of different value to be selected and applied to said second signal;

e.) means for cross-correlating said first and delayed second signals to generate a third signal, and said cross-correlating means averaging any spurious signals caused by noise;

f.) means for applying said third signal to said delay means to produce a delay of proper value for maximizing said third signal;

g.) an alarm means coupled to said third signal, h.) whereby when a certain magnitude of said delay exceeds a pre-determined value, said alarm means is activated and a person is deemed to be impaired due to said drowsiness, inattention, or substance abuse.

6. An alert monitor system in accordance with claim 5 wherein said juxtaposed means includes an appliance with ear pieces for positioning around the face.

7. An alert monitor system in accordance with claim 6 wherein said appliance further includes sensory means placed in contact with the skin above and below the eye.

8. An alert monitor system in accordance with claim 7 wherein said appliance further includes an angular position sensor which is mounted upon said ear pieces and having a sensing axis along a horizontal axis about which the eyes rotate in response to a vertical motion of the head.

9. An alert monitoring system for use by a person in order to detect drowsiness, inattention, or substance abuse comprising, a.) means juxtaposed to certain facial areas for respectively detecting positions of the person's eyes and head when the eyes are fixating upon a viewed object;

b.) said juxtaposed means allowing said person to freely move in all directions, and c.) said juxtaposed means including means for generating first and second analog signals respectively based upon a fixation of the eyes upon said viewed object as well as the position of the head with respect to the fixation, and a lag occurring in the first signal with respect to the second signal;

d.) means for converting said first and second analog signals into digital form;

e.) means for receiving said digitized first signal, and said digitized second signal after passing through a variable delay means, to cross-correlate said signals, said receiving means generating a cross-correlated third signal to average out spurious background noise;

f.) means for receiving said third signal and generating a fourth signal for selecting and modifying said variable delay means and for increasing or decreasing the delay applied to said second signal to minimize said lag;

g.) means coupled to said modifying means to determine whether said cross-correlated third signal is within or outside a defined limit upon receiving respective second and fourth signals;

h.) whereby if the delay in a response of the eye is outside said defined limit, a person is deemed to be impaired due to said drowsiness, inattention, or substance abuse.

10. An alert monitoring system in accordance with claim 9 wherein said means for receiving said first and second digitized signals comprises a main correlator and a peak location correlator.

11. An alert monitor system in accordance with claim 9 wherein said analog signals from said eye and head positions are coupled to respective first and second analog-to-digital converters after passing through filter means.

12. An alert monitor system in accordance with claim 9 wherein said receiving means comprises a comparison means for monitoring amplitudes of said first and second digitized signals and the fourth signal of said modifying means being applied to said variable delay means to select the amplitude peak nearest to zero delay.

13. An alert monitor system in accordance with claim 12 wherein said variable delay means comprises a variable length shift register.

* * * * *